US005627155A

United States Patent [19]

Moore et al.

[11] Patent Number: 5,627,155

[45] Date of Patent: May 6, 1997

[54] BCRF1 PROTEINS AS INHIBITORS OF INTERFERON-γ

[75] Inventors: Kevin W. Moore, Palo Alto; Robert A. Kastelein, Redwood City, both of Calif.

[73] Assignee: Schering Corporation, Kenilworth, N.J.

[21] Appl. No.: 450,749

[22] Filed: May 26, 1995

Related U.S. Application Data

[63] Continuation of Ser. No. 343,297, Nov. 22, 1994, abandoned, which is a continuation of Ser. No. 132,679, Oct. 6, 1993, abandoned, which is a continuation of Ser. No. 16,175, Jan. 19, 1993, abandoned, which is a continuation of Ser. No. 830,763, Feb. 4, 1992, abandoned, which is a continuation of Ser. No. 453,931, Dec. 20, 1989, abandoned.

[51] Int. Cl.[6] .......................... A61K 38/20; A61K 38/16; C07K 14/05; C07K 14/54

[52] U.S. Cl. .................................... 514/12; 514/2; 514/8; 424/85.1; 424/85.2; 424/85.5; 530/350; 530/351; 530/826; 930/141

[58] Field of Search .................... 514/2, 12, 8; 424/85.1, 424/85.2, 85.5; 530/350, 351, 826

[56] References Cited

FOREIGN PATENT DOCUMENTS

A0173254 3/1986 European Pat. Off. .

OTHER PUBLICATIONS

R. Baer, et al., "DNA sequence and expression of the B95–8 Epstein–Barr virus genome," *Nature*, 310:207–211, Jul. 19, 1984.

Andrew G.D. Bean, et al., "Interleukin 10 Protects Mice against Staphylococcal Enterotoxin B–Induced Lethal Shock," *Infection and Immunity*, 61(10):4937–4939, Nov. 1993.

Rene de Waal Malefyt, et al., "Interleukin 10(IL–10) Inhibits Cytokine Synthesis by Human Monocytes: An Autoregulatory Role of IL–10 Produced by Monocytes," *J. Exp. Med.*, 174:1209–1220, Nov. 1991.

Joakim Dillner and Bengt Kallin, "The Epstein–Barr Virus Proteins," *Advances in Cancer Research*, 50:95–158, 1988.

David F. Fiorentino, et al., "IL–10 Inhibits Cytokine Production By Activated Macrophages," *The Journal of Immunology*, 147 (11):3815–3822, Dec. 1, 1991.

Maureen Howard, et al., "Interleukin 10 Protects Mice from Lethal Endotoxemia," *J. Exp. Med.*, 117:1205–1211, Apr. 1993.

Jay B. Horowitz, et al., "Autocrine growth inhibition of a cloned line of helper T. cells," *Proc. Natl. Acad. Sci. USA*, 83:1886–1890, Mar. 1986.

Di–Hwei Hsu, et al., "Differential effects of IL–4 and IL–10 on IL–2–induced IFN–γ synthesis and lymphokine–activated killer activity," *J. of Immunol.*, 6:663–669, Jan. 27, 1992.

Di–Hwei Hsu, et al., "Expression of Interleukin–10 Activity by Epstein–Barr Virus Protein BCRF1," *Science*, 250:830–832, Nov. 9, 1990.

Graham S. Hudson, et al., "The Short Unique Region of the B95–8 Epstein–Barr Virus Genome," *Virology*, 147:81–98, 1985.

Arnaud Marchant, et al., "Interleukin–10 controls interferon–γ and tumor necrosis factor production during experimental endotoxemia," *Eur. J. Immunol.*, 24:1167–1171, 1994.

Hugh O. McDevitt, "The Molecular Basis of Autoimmunity," *Clinical Research*, 34:163–175, 1985.

Kevin W. Moore, et al., "Homology of Cytokine Synthesis Inhibitory Factor (IL–10) to the Epstein–Barr Virus Gene BCRF1," *Science*, 248:1230–1234, Jun. 8, 1990.

David A. Thorley–Lawson, "Immunological responses to Epstein–Barr virus infection and the pathogenesis of EBV–induced diseases," *Biochimica et Biophysica Acta*, 948:263–286, 1988.

Giovanna Tosato, "The Epstein–Barr Virus and the Immune System," *Advances in Cancer Research*, 49:75–125, 1987.

P. Vieira, et al., "Isolation and expression of human cytokine synthesis inhibitory factor cDNA clones: Homology to Epstein–Barr virus open reading frame BCRF1," *Proc. Natl. Acad. Sci. USA*, 88:1172–1176, Feb. 1991.

Kondo et al. (1994) "Interleukin–10 inhibits the elicitation phase of allergic contact hypersensitivity" J. Investig. Dermatol. 103:811–814.

David F. Fiorentino, et al., "Two types of mouse T helper cell IV. Thy 2 clones secrete a factor that inhibits cytokine production by Th1 clones," *Journal of Experimental Medicine*, 170:2081–2095, Dec. 1989.

Ning Fei Go, et al., "Interleukin 10, a novel B cell stimulatory factor: Unresponsiveness of X chromosome–linked immunodeficiency B cells," *Journal of Experimental Medicine*, 172(6):1625–1631, Dec. 1, 1990.

Gunnar von Heijne, "A new method for predicting signal sequence cleavage sites," *Nucleic Acids Research*, 14(11):4683–4690, 1986.

*Primary Examiner*—Robert A. Wax
*Assistant Examiner*—G. E. Bugaisky
*Attorney, Agent, or Firm*—Stephen C. Macevicz; Edwin P. Ching; Karen B. Dow

[57] ABSTRACT

BCRF1 proteins are provided for treating conditions associated with excessive production of IFN-γ. Also provided are expression vectors for producing BCRF1 proteins. Compositions of the invention are useful in treating a variety of disorders, including allergy, psoriasis, tissue rejection, and MHC-linked autoimmune diseases.

21 Claims, 2 Drawing Sheets

BCRF1 PROTEINS AS INHIBITORS OF INTERFERON-γ

CROSS-REFERENCE TO RELATED APPLICATIONS

This is a continuation of application Ser. No. 08/343,297, filed Nov. 22, 1994, now abandoned, which is a continuation of application U.S. Ser. No. 08/132,679, filed Oct. 6, 1993, now abandoned which is a continuation of application Ser. No. 08/016,175, filed Jan. 19, 1993, now abandoned, which is a continuation of application Ser. No. 07/830,763, filed Feb. 4, 1992, now abandoned, which is a continuation of application Ser. No. 07/453,931, filed Dec. 20, 1989, now abandoned.

FIELD OF THE INVENTION

The invention relates generally to methods and compositions for treating diseases associated with excessive interferon-γ (IFN-γ) production, and more particularly, to methods and compositions employing the Epstein-Barr virus (EBV) protein BCRF1 for effectively reducing levels of IFN-γ.

BACKGROUND

The immune system comprises a highly interactive complex of tissues, cell types, and soluble factors. Recently, it has been suggested that several diseases and immune disorders may be associated with imbalances among certain components of the immune system, particularly cytokines, e.g. Mosmann et al, Ann. Rev. Immunol., Vol. 7, pgs. 145–173 (1989); Cher et al, J. Immunol., Vol. 138, pgs. 3688–3694 (1987); Mosmann et al, Immunol. Today, Vol. 8, pgs. 223–227 (1987); and Heinzel et al, J. Exp. Med., Vol. 169, pgs. 59–72 (1989).

For example, a large body of evidence suggests that excessive production of gamma interferon (IFN-γ) is responsible for major histocompatibility complex (MHC) associated autoimmune diseases, Hooks et al, *New England J. Med.*, Vol. 301, pgs. 5–8 (1979) (elevated serum levels of IFN-γ correlated with autoimmunity); Basham et al, *J. Immunol.*, Vol. 130, pgs. 1492–1494 (1983) (IFN-γ can increase MHC gene product expression); Battazzo et al, Lancet, pgs. 1115–1119 (Nov. 12, 1983) (aberrant MHC gene product expression correlated with some forms of autoimmunity); Hooks et al, *Ann. N.Y. Acad. Sci.*, Vol., pgs. 21–32 (1980) (higher IFN-γ levels correlated to greater severity of disease in SLE patients, and histamine-release enhancing activity of interferon can be inhibited by anti-interferon sera); Jacob et al, J. Exp. Med., Vol. 166, pgs. 798–803 (1987) (amelioration and delay of onset of disease conditions in mouse models of systemic lupus erythematosus by blocking anti-IFN-γ monoclonal antibodies); and Iwatani et al, *J. Clin. Endocrin. and Metabol.*, Vol. 63, pgs. 695–708 (1986) (anti-IFN-γ monoclonal antibody eliminated the ability of leucoagglutinin-stimulated T cells to induce HLA-DR expression). It has been hypothesized that excess IFN-γ causes the inappropriate expression of MHC gene products which, in turn, causes autoimmune reactions against the tissues whose cells are inappropriately expressing the MHC products and displaying autoantigens in the context of the products. Thus, it has been suggested that reducing IFN-γ levels in autoimmune patients, e.g. by administering IFN-γ antagonists, could have beneficial effects, e.g. McDevitt, Clin. Res., Vol. 34, pgs. 163–175 (1985).

In addition to the above evidence, IFN-γ may also play a role in allergy by its ability to increase the number and density of Fcε receptors on monocytes, it has been implicated in the pathogenesis of sarcoidosis and psoriasis, and it is believed to augment cell-mediated immunity, which plays a major role in tissue rejection in allogenic transplant patients.

In view of the above, the availability of compounds capable of reducing IFN-γ levels would be highly advantageous for treatment of diseases associated with inappropriate immune responses, such as some parasitic diseases, allergy, and MHC associated immune disorders, including rheumatoid arthritis, systemic lupus erythematosus (SLE), myasthenia gravis, insulin-dependent diabetes mellitus, thyroiditis, and the like.

SUMMARY OF THE INVENTION

The invention relates to methods and compositions for treating diseases associated with high levels of IFN-γ production. The method of the invention comprises the step of administering a disease-controlling amount of a BCRF1, a protein derived from the Epstein-Barr virus. The invention further includes expression vectors for producing recombinant BCRF1, purified BCRF1, and pharmaceutical compositions for use with the method. Preferably, the BCRF1 used with the invention is selected from the group of mature polypeptides of the open reading frame defined by the following amino acid sequence:

| Formula I |
| --- |
| Met—Glu—Arg—Arg—Leu—Val—Val—Thr—Leu—Gln—Cys—<br>Leu—Val—Leu—Leu—Tyr—Leu—Ala—Pro—Glu—Cys—Gly—<br>Gly—Thr—Asp—Gln—Cys—Asp—Asn—Phe—Pro—Gln—Met—<br>Leu—Arg—Asp—Leu—Arg—Asp—Ala—Phe—Ser—Ara—Val—<br>Lys—Thr—Phe—Phe—Gln—Thr—Lys—Asp—Glu—Val—Asp—<br>Asn—Leu—Leu—Leu—Lys—Glu—Ser—Leu—Leu—Glu—Asp—<br>Phe—Lys—Gly—Tyr—Leu—Gly—Cys—Gln—Ala—Leu—Ser—<br>Glu—Met—Ile—Gln—Phe—Tyr—Leu—Glu—Glu—Val—Met—<br>Pro—Gln—Ala—Glu—Asn—Gln—Asp—Pro—Glu—Ala—Lys—<br>Asp—His—Val—Asn—Ser—Leu—Gly—Glu—Asn—Leu—Lys—<br>Thr—Leu—Arg—Leu—Arg—Leu—Arg—Arg—Cys—His—Arg—<br>Phe—Leu—Pro—Cys—Glu—Asn—Lys—Ser—Lys—Ala—Val—<br>Glu—Gln—Ile—Lys—Asn—Ala—Phe—Asn—Lys—Leu—Gln—<br>Glu—Lys—Gly—Ile—Tyr—Lys—Ala—Met—Ser—Glu—Phe—<br>Asp—Ile—Phe—Ile—Asn—Tyr—Ile—Glu—Ala—Tyr—Met—<br>Thr—Ile—Lys—Ala—Arg |

Formula I wherein the above abbreviations indicate the L forms of the amino acids, and the amino acids are listed starting from the N-terminus.

DETAILED DESCRIPTION OF THE INVENTION

Figure 1:
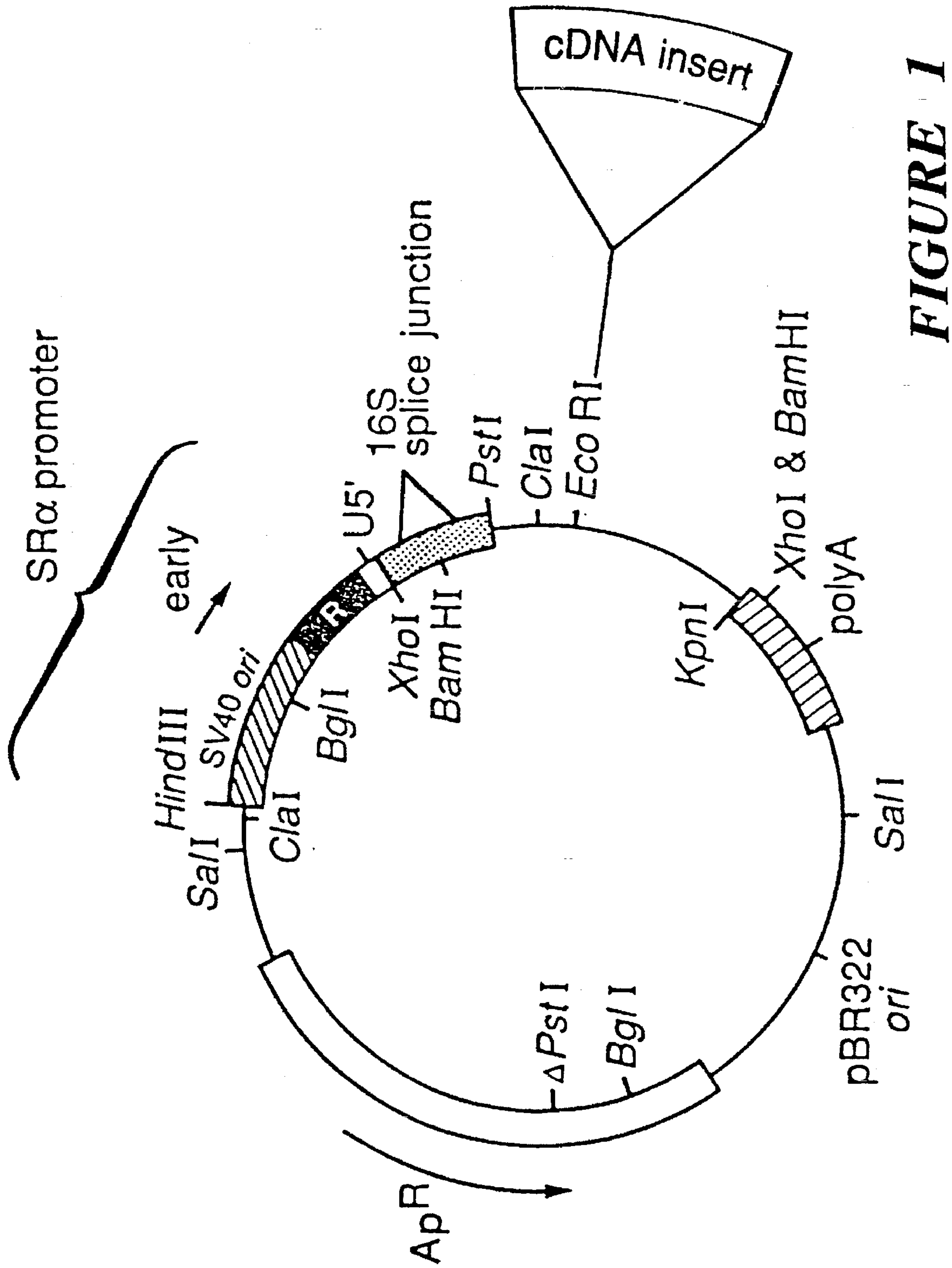
FIG. 1 is a diagrammatic illustration of a mammalian expression vector useful in the production of BCRF1.

The invention relates to methods and compositions for treating diseases associated with excessive IFN-γ production. The invention is based in part on the discovery that the nucleic acid sequence encoding a recently discovered protein, designated cytokine synthesis inhibitory factor, possesses a high degree of homology with the EBV BCRF1 open reading frame. EBV is a human herpesvirus endemic in all human populations, and has been associated with several diseases, e.g. Dillner et al, Adv. Cancer Res., Vol 50, pgs. 95–158 (1988); Thorley-Lawson, Biochim. Biophys. Acta, Vol. 948, pgs. 263–286 (1988); and Tasato, Adv. Cancer Res., Vol. 49, pgs. 75–125 (1987). EBV has a double-stranded DNA genome of about 172 kilobases, Baer et al, Nature, Vol. 310, pgs. 207–211 (1984). The genome contains many open reading frames apparently corresponding to proteins produced by EBV, one of which is BCRF1.

The invention includes mature polypeptides, or proteins, of the BCRF1 open reading frame. For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g. von Heijne, Nucleic Acids Research, Vol. 14, pgs. 4683–4690 (1986), and the precise amino acid composition of the signal peptide does not appear to be critical to its function, e.g. Randall et al, Science, Vol. 243, pgs. 1156–1159 (1989); Kaiser et al, Science, Vol. 235, pgs. 312–317 (1987). Consequently, mature proteins are readily expressed by vectors encoding signal peptides quite different than that encoded by the open reading frame defined by Formula I.

A wide range of expression systems (i.e. host-expression vector combinations) can be used to produce the proteins of the invention. Possible types of host cells include, but are not limited to, bacterial, yeast, insect, mammalian, and the like. Many reviews are available which provide guidance for making choices and/or modifications of specific expression systems, e.g. to name a few, de Boer and Shepard, "Strategies for Optimizing Foreign Gene Expression in *Escherichia coli*," pgs. 205–247, in Kroon, ed. Genes: Structure and Expression (John Wiley & Sons, New York, 1983), review several *E. coli* expression systems; Kucherlapati et al., Critical Reviews in Biochemistry, Vol. 16, Issue 4, pgs. 349–379 (1984), and Banerji et al., Genetic Engineering, Vol. 5, pgs. 19–31 (1983) review methods for transfecting and transforming mammalian cells; Reznikoff and Gold, eds., Maximizing Gene Expression (Butterworths, Boston, 1986) review selected topics in gene expression in *E. coli*, yeast, and mammalian cells; and Thilly, Mammalian Cell Technology (Butterworths, Boston, 1986) reviews mammalian expression systems. Likewise, many reviews are available which describe techniques and conditions for linking and/or manipulating specific cDNAs and expression control sequences to create and/or modify expression vectors suitable for use with the present invention, e.g. Sambrook et al., Molecular Cloning: A Laboratory Manual, 2nd Ed. (Cold Spring Harbor Laboratory, N.Y., 1989).

An *E. coli* expression system is disclosed by Riggs in U.S. Pat. No. 4,431,739, which is incorporated by reference. Particularly useful prokaryotic promoters for high expression in *E. coli* are the tac promoter, disclosed by de Boer in U.S. Pat. No. 4,551,433, which is incorporated herein by reference, and the $p_L$ promoter, disclosed by Remaut et al, Gene, Vol 15, pgs. 81–93 (1981), which is incorporated by reference. Secretion expression vectors are also available for *E. coli* hosts. Particularly useful are the pIN-III-ompA vectors, disclosed by Ghrayeb et al., in EMBO J., Vol. 3, pgs. 2437–2442 (1984), in which the cDNA to be transcribed is fused to the portion of the *E. coli* OmpA gene encoding the signal peptide of the ompA protein which, in turn, causes the mature protein to be secreted into the periplasmic space of the bacteria. U.S. Pat. Nos. 4,336,336; 4,411,994; 4,332,892; and 4,338,397 also disclose secretion expression vectors for prokaryotes. Accordingly, these references are incorporated by reference. Numerous stains of bacteria are suitable hosts for prokaryotic expression vectors including strains of *E. coli*, such as W3110 (ATCC No. 27325), JA221, C600, ED767, DH1, LE392, HB101, X1776 (ATCC No. 31244), X2282, RR1 (ATCC No. 31343) MRCI; strains of *Bacillus subtilus*; and other enterobacteriaceae such as *Salmonella typhimurium* or *Serratia marcescens*, and various species of Pseudomonas. General methods for deriving bacterial strains, such as *E. coli* K12 X1776, useful in the expression of eukaryotic proteins is disclosed by Curtis III in U.S. Pat. No. 4,190,495. Accordingly this patent is incorporated by reference. In addition to prokaryotic and eukaryotic microorganisms, expression systems comprising cells derived from multicellular organism may also be used to produce proteins of the invention. Of particular interest are mammalian expression systems because their posttranslational processing machinery is more likely to produce biologically active mammalian proteins. Several DNA tumor viruses have been used as vectors for mammalian hosts. Particularly important are the numerous vectors which comprise SV40 replication, transcription, and/or translation control sequences coupled to bacterial replication control sequences, e.g. the pcD vectors developed by Okayama and Berg, disclosed in Mol. Cell. Biol., Vol. 2, pgs. 161–170 (1982) and Mol. Cell. Biol., Vol. 3, pgs. 280–289 (1983), and improved by Takebe et al, Mol. Cell. Biol., Vol. 8, pgs. 466–472 (1988). Accordingly, these references are incorporated herein by reference. Other SV40-based mammalian expression vectors include those containing adenovirus regulatory elements, disclosed by Kaufman and Sharp, in Mol. Cell. Biol., Vol. 2, pgs. 1304–1319 (1982), and Clark et al., in U.S. Pat. No. 4,675,285, both of which are incorporated herein by reference. Monkey cells are usually the preferred hosts for the above vectors. Such vectors containing the SV40 ori sequences and an intact A gene can replicate autonomously in monkey cells (to give higher copy numbers and/or more stable copy numbers than nonautonomously replicating plasmids). Moreover, vectors containing the SV40 ori sequences without an intact A gene can replicate autonomously to high copy numbers (but not stably) in COS7 monkey cells, described by Gluzman, Cell, Vol. 23, pgs. 175–182 (1981) and available from the ATCC (accession no. CRL 1651). The above SV40-based vectors are also capable of transforming other mammalian cells, such as mouse L cells, by integration into the host cell DNA.

The biological activity of the BCRF1s of the invention are readily determined in IFN-γ inhibition assays. Such assays require a cell line or cell population that synthesizes IFN-γ. Conveniently, peripheral blood lymphocytes (PBLs) that have been stimulated with a mitogen such as phytohemagglutinin (PHA) can serve as such a cell population. Roughly, the assay works as follows: The PHA-stimulated PBLs are divided into two equal parts. To one part, a sample containing a BCRF1 is added. The other part serves as a control. After several days the supernatants of both cultures are tested for IFN-γ. This is conveniently done with a standard ELISA assay using commercially available monoclonal and polyclonal antibodies for IFN-γ, e.g. Genzyme, Inc., (Boston, Mass.). Alternatively, the readout of the assay can be the amount of IFN-γ mRNA transcribed, for example, as measured by RNA blotting, PCR, or like methodology. PBLs are obtained using standard techniques, e.g. Mishell et al, eds., *Selected Methods in Cellular Immunology* (Freeman, N.Y., 1980).

When polypeptides of the present invention are expressed in soluble form, for example as a secreted product of transformed yeast or mammalian cells, they can be purified according to standard procedures of the art, including steps of ammonium sulfate precipitation, ion exchange chromatography, gel filtration, electrophoresis, affinity chromatography, and/or the like, e.g. "Enzyme Purification and Related Techniques," Methods in Enzymology, 22:233–577 (1977), and Scopes, Protein Purification: Principles and Practice (Springer-Verlag, New York, 1982) provide guidance in such purifications. Likewise, when polypeptides of the invention are expressed in insoluble form, for example as aggregates, inclusion bodies or the like, they can be purified by standard procedures in the art, including separating the inclusion bodies from disrupted host cells by centrifugation, solubilizing the inclusion bodies with chaotropic and reducing agents diluting the solubilized mixture, and lowering the concentration of chaotropic agent and reducing agent so that the polypeptide takes on a biologically active conformation. The latter procedures are disclosed in the following references, which are incorporated by reference: Winkler et al, Biochemistry, 25: 4041–4045 (1986); Winkler et al, Biotechnology, 3: 992–998 (1985); Koths et al, U.S. Pat. No. 4,569,790; and European patent applications 86306917.5 and 86306353.3.

As used herein "effective amount" means an amount sufficient to ameliorate a symptom of an disease condition mediated by excessive IFN-γ. The effective amount for a particular patient may vary depending on such factors as the state of the disease condition being treated, the overall health of the patient, method of administration, the severity of side-effects, and the like. Generally, BCRF1 is administered as a pharmaceutical composition comprising an effective amount of BCRF1 and a pharmaceutical carrier. A pharmaceutical carrier can be any compatible, non-toxic substance suitable for delivering the compositions of the invention to a patient. Generally, compositions useful for parenteral administration of such drugs are well known, e.g. Remington's Pharmaceutical Science, 151h Ed. (Mack Publishing Company, Easton, Pa. 1980). Alternatively, compositions of the invention may be introduced into a patient's body by implantable drug delivery system, e.g. Urquhart et at., Ann. Rev. Pharmacol. Toxicol., Vol. 24, pgs. 199–236 (1984); Lewis, ed. Controlled Release of Pesticides and Pharmaceuticals (Plenum Press, New York, 1981); U.S. Pat. No. 3,773,919; U.S. Pat. No. 3,270,960; and the like.

When administered parenterally, the BCRF1 is formulated in a unit dosage injectable form (solution, suspension, emulsion) in association with a pharmaceutical carrier. Such carriers are inherently nontoxic and nontherapeutic. Examples of such carriers are normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. BCRF1 is preferably formulated in purified form substantially free of aggregates and other proteins at a concentration in the range of about 5 to 20 μg/ml. Preferably, BCRF1 is administered by continuous infusion so that an amount in the range of about 50–800 μg is delivered per day (i.e. about 1–16 μg/kg/day). The daily infusion rate may be varied based on monitoring of side effects, blood cell counts, and the like.

EXAMPLES

Example 1

Expression of BCRF1 in COS 7 Monkey Cells

A gene encoding the open reading frame for BCRF1 was amplified by polymerase chain reaction using primers that allowed later insertion of the amplified fragment into an Eco RI-digested pcD(SRα) vector (FIG. 1). The coding strand of the inserted fragment is shown below (the open reading frame being given in capital letters).

| | | | | |
|---|---|---|---|---|
| aattcATGGA | GCGAAGGTTA | GTGGTCACTC | TGCAGTGCCT | GGTGCTGCTT |
| TACCTGGCAC | CTGAGTGTGG | AGGTACAGAC | CAATGTGACA | ATTTTCCCCA |
| GACCTAAGAG | ATGCCTTCAG | TCGTGTTAAA | ACCTTTTTCC | AGACAAAGGA |
| CGAGGTAGAT | AACCTTTTGC | TCAAGGAGTC | TCTGCTAGAG | GACTTTAAGG |
| ATGCCAGGCC | CTGTCAGAAA | TGATCCAATT | CTACCTGGAG | GAAGTCATGC |
| CACAGGCTGA | AACCAGGAC | CCTGAAGCCA | AAGACCATGT | CAATTCTTTG |
| GGTGAAAATC | TAAAGACCCT | ACGGCTCCGC | CTGCGCAGGT | GCCACAGGTT |
| CCTGCCGTGT | GAGAACAAGA | GTAAAGCTGT | GGAACAGATA | AAAAATGCCT |
| TTAACAAGCT | GCAGGAAAAA | GGAATTTACA | AAGCCATGAG | TGAATTTGAC |
| ATTTTTATTA | ACTACATAGA | AGCATACATG | ACAATTAAAG | CCAGGTGAg |

Clones carrying the insert in the proper orientation were identified by expression of BCRF1 and/or the electrophoretic pattern of restriction digests. One such vector carrying the BCRF1 gene was designated pBCRFI(SRcα) and was deposited with the ATCC under accession number 68193. pBCRFI(SRcα) was amplified in *E. coli* MC1061, isolated by standard techniques, and used to transfect COS 7 monkey cells as follows: One day prior to transfection, approximately $1.5\times10^6$ COS 7 monkey cells were seeded onto individual 100 mm plates in Dulbecco's modified Eagle medium (DME) containing 5% fetal calf serum (FCS) and 2 mM glutamine. To perform the transfection, COS 7 cells were removed from the dishes by incubation with trypsin, washed twice in serum-free DME, and suspended to $10^7$ cells/ml in serum-free DME. A 0.75 ml aliquot was mixed with 20 μg DNA and transferred to a sterile 0.4 cm electroporation cuvette. After 10 minutes, the cells were pulsed at 200 volts, 960 μF in a BioRad Gene Pulser unit. After another 10 minutes, the cells were removed from the cuvette and added to 20 ml of DME containing 5% FCS, 2 mM glutamine, penicillin, streptomycin, and gentamycin. The mixture was aliquoted to four 100 mm tissue culture dishes. After 12–24 hours at 37° C., 5% $CO_2$, the medium was replaced with similar medium containing only 1% FCS and the incubation continued for an additional 72 hours at 37° C., 5% $CO_2$, after which the medium was collected and assayed for its ability to inhibit IFN-γ synthesis.

10 ml aliquots of freshly isolated PBLs (about $2\times10^6$ cells/ml) were incubated at 37° C. with PHA (100 ng/ml) in medium consisting of (i) 90% DME supplemented with 5% FCS and 2 mM glutamine, and (ii) 10% supernatant from COS 7 cells previously transfected with pBCRF1(SRα). After 24 hours the cells and supernatants were harvested to assay for the presence of either IFN-γ mRNA or IFN-γ protein, respectively. Controls were treated identically, except that the 10% supernatant was from COS 7 cultures previously transfected with a plasmid carrying an unrelated cDNA insert. The BCRF1-treated samples exhibited about a 50% inhibition of IFN-γ synthesis relative to the controls.

Example 2

Expression of BCRF1 in *Escherichia coli*

A gene encoding a mature BCRF1 of the sequence given below may be expressed in *E. coli.*

Thr—Asp—Gln—Cys—Asp—Asn—Phe—Pro—Gln—Met—Leu—
Arg—Asp—Leu—Arg—Asp—Ala—Phe—Ser—Arg—Val—Lys—
Thr—Phe—Phe—Gln—Thr—Lys—Asp—Glu—Val—Asp—Asn—
Leu—Leu—Leu—Lys—Glu—Ser—Leu—Leu—Glu—Asp—Phe—
Lys—Gly—Tyr—Leu—Gly—Cys—Gln—Ala—Leu—Ser—Glu—
Met—Ile—Gln—Phe—Tyr—Leu—Glu—Glu—Val—Met—Pro—
Gln—Ala—Glu—Asn—Gln—Asp—Pro—Glu—Ala—Lys—Asp—
His—Val—Asn—Ser—Leu—Gly—Glu—Asn—Leu—Lys—Thr—
Leu—Arg—Leu—Arg—Leu—Arg—Arg—Cys—His—Arg—Phe—
Leu—Pro—Cys—Glu—Asn—Lys—Ser—Lys—Ala—Val—Glu—
Gln—Ile—Lys—Asn—Ala—Phe—Asn—Lys—Leu—Gln—Glu—
Lys—Gly—Ile—Tyr—Lys—Ala—Met—Ser—Glu—Phe—Asp—
Ile—Phe—Ile—Asn—Tyr—Ile—Glu—Ala—Tyr—Met—Thr—
Ile—Lys—Ala—Arg.

The cDNA insert of pBCRF1(SRα) is recloned into an M13 plasmid where it is altered twice by site-directed mutagenesis: first to form a Cla I site at the 5' end of the coding region for the mature BCRF1 polypeptide, and second to form a Barn HI site at the 3' end of the coding region for the mature BCRF1 polypeptide. The mutated sequence is then readily inserted into the TRPC11 expression vector described below.

Figure 2:
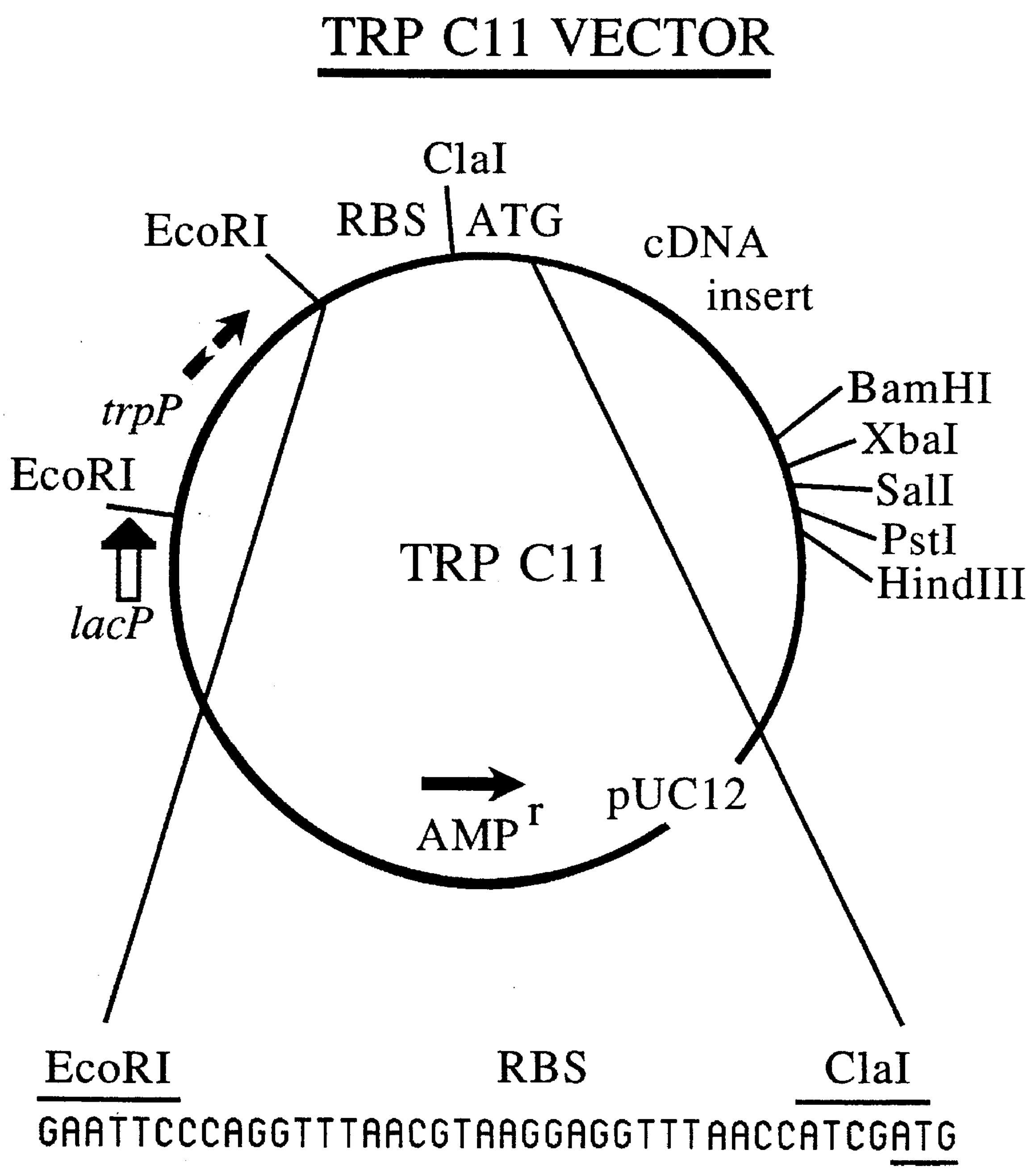
FIG. 2 is a diagrammatic illustration of a bacterial expression vector useful in the production of BCRF1.

The TRPC11 vector was constructed by ligating a synthetic consensus RBS fragment to ClaI linkers (ATGCAT) and by cloning the resulting fragments into ClaI restricted pMT11hc (which had been previously modified to contain the ClaI site). pMT11hc is a small (2.3 kilobase) high copy, $AMP^R$, $TET^S$ derivative of pBR322 that bears the πVX plasmid EcoRI-HindIII polylinker region. (πVX is described by Maniatis et al., Molecular Cloning: A Laboratory Manual, Cold Spring Harbor Laboratory, 1982). This was modified to contain the ClaI site by restricting pMT11hc with EcoRI and BamHI, filling in the 5 resulting sticky ends and ligating with ClaI linker (CATCGATG), thereby restoring the EcoRI and BamHI sites and replacing the Sinai site with a ClaI site. One transformant from the TRPC11 construction had a tandem RBS sequence flanked by ClaI sites. One of the ClaI sites and part of the second copy of the RBS sequence were removed by digesting this plasmid with PstI, treating with Bal31 nuclease, restricting with EcoRI and treating with T4 DNA polymerase in the presence of all four deoxynucleotide triphosphates. The resulting 30–40 bp fragments were recovered via PAGE and cloned into SmaI restricted pUC12. A 248 bp *E. coli* trpP-bearing EcoRI fragment derived from pKC101 (described by Nichols et al. in Methods in Enzymology, Vol. 101, pg. 155 (Academic Press, N.Y. 1983)) was then cloned into the EcoRI site to complete the TRPC11 construction, which is illustrated in FIG. 2. TRPC11 is employed as a vector for BCRF1 by first digesting it with ClaI and Bam HI, purifying it, and then mixing it in a standard ligation solution with the ClaI-Bam HI fragment of the M13 containing the nucleotide sequence coding for the mature BCRF1. The insert-containing TRPC11, referred to as TRPC11-BCRF1, is propagated in *E. coli* K12 strain JM101, e.g. available from the ATCC under accession number 33876.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended, hereto.

Applicants have deposited *E. coli* MC1061 carrying pBCRF1(SRα) with the American Type Culture Collection, Rockville, Md., USA (ATCC), under accession number 68193. This deposit was made under conditions as provided under ATCC's agreement for Culture Deposit for Patent Purposes, which assures that the deposit will be made available to the US Commissioner of Patents and Trademarks pursuant to 35 USC 122 and 37 CFR 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

We claim:

1. A method of treating an individual to control a disease associated with excessive interferon-γ production, the method comprising the step of administering a therapeutically effective amount of BCRF1.

2. The method of claim 1 wherein said BCRF1 is selected from the group of mature proteins of an open reading frame defined by the amino acid sequence:

Met—Glu—Arg—Arg—Leu—Val—Val—Thr—Leu—Gln—Cys—
Leu—Val—Leu—Leu—Tyr—Leu—Ala—Pro—Glu—Cys—Gly—
Gly—Thr—Asp—Gln—Cys—Asp—Asn—Phe—Pro—Gln—Met—
Leu—Arg—Asp—Leu—Arg—Asp—Ala—Phe—Ser—Ara—Val—
Lys—Thr—Phe—Phe—Gln—Thr—Lys—Asp—Glu—Val—Asp—
Asn—Leu—Leu—Leu—Lys—Glu—Ser—Leu—Leu—Glu—Asp—
Phe—Lys—Gly—Tyr—Leu—Gly—Cys—Gln—Ala—Leu—Ser—
Glu—Met—Ile—Gln—Phe—Tyr—Leu—Glu—Glu—Val—Met—
Pro—Gln—Ala—Glu—Asn—Gln—Asp—Pro—Glu—Ala—Lys—
Asp—His—Val—Asn—Ser—Leu—Gly—Glu—Asn—Leu—Lys—
Thr—Leu—Arg—Leu—Arg—Leu—Arg—Arg—Cys—His—Arg—
Phe—Leu—Pro—Cys—Glu—Asn—Lys—Ser—Lys—Ala—Val—
Glu—Gln—Ile—Lys—Asn—Ala—Phe—Asn—Lys—Leu—Gln—
Glu—Lys—Gly—Ile—Tyr—Lys—Ala—Met—Ser—Glu—Phe—
Asp—Ile—Phe—Ile—Asn—Tyr—Ile—Glu—Ala—Tyr—Met—
Thr—Ile—Lys—Ala—Arg.

3. The method of claim 2 wherein said step of administering includes intravenous delivery of an amount of said BCRF1 in the range of about 1–10 mg/kg body weight of said individual per day.

4. The method of claim 2 wherein said mature protein is defined by the amino acid sequence:

Thr—Asp—Gln—Cys—Asp—Asn—Phe—Pro—Gln—Met—Leu—
Arg—Asp—Leu—Arg—Asp—Ala—Phe—Ser—Arg—Val—Lys—
Thr—Phe—Phe—Gln—Thr—Lys—Asp—Glu—Val—Asp—Asn—
Leu—Leu—Leu—Lys—Glu—Ser—Leu—Leu—Glu—Asp—Phe—
Lys—Gly—Tyr—Leu—Gly—Cys—Gln—Ala—Leu—Ser—Glu—
Met—Ile—Gln—Phe—Tyr—Leu—Glu—Glu—Val—Met—Pro—
Gln—Ala—Glu—Asn—Gln—Asp—Pro—Glu—Ala—Lys—Asp—
His—Val—Asn—Ser—Leu—Gly—Glu—Asn—Leu—Lys—Thr—
Leu—Arg—Leu—Arg—Leu—Arg—Arg—Cys—His—Arg—Phe—
Leu—Pro—Cys—Glu—Asn—Lys—Ser—Lys—Ala—Val—Glu—
Gln—Ile—Lys—Asn—Ala—Phe—Asn—Lys—Leu—Gln—Glu—
Lys—Gly—Ile—Tyr—Lys—Ala—Met—Ser—Glu—Phe—Asp—

-continued

| |
|---|
| Ile—Phe—Ile—Asn—Tyr—Ile—Glu—Ala—Tyr—Met—Thr—Ile—Lys—Ala—Arg. |

5. The method of claim 1, wherein said administering is parenteral.

6. A pharmaceutical composition comprising an effective amount of BCRF1 and a pharmaceutical carrier.

7. The composition of claim 6 wherein the BCRF1 is defined by the amino acid sequence:

| |
|---|
| Thr—Asp—Gln—Cys—Asp—Asn—Phe—Pro—Gln—Met—Leu—Arg—Asp—Leu—Arg—Asp—Ala—Phe—Ser—Arg—Val—Lys—Thr—Phe—Phe—Gln—Thr—Lys—Asp—Glu—Val—Asp—Asn—Leu—Leu—Leu—Lys—Glu—Ser—Leu—Leu—Glu—Asp—Phe—Lys—Gly—Tyr—Leu—Gly—Cys—Gln—Ala—Leu—Ser—Glu—Met—Ile—Gln—Phe—Tyr—Leu—Glu—Glu—Val—Met—Pro—Gln—Ala—Glu—Asn—Gln—Asp—Pro—Glu—Ala—Lys—Asp—His—Val—Asn—Ser—Leu—Gly—Glu—Asn—Leu—Lys—Thr—Leu—Arg—Leu—Arg—Leu—Arg—Arg—Cys—His—Arg—Phe—Leu—Pro—Cys—Glu—Asn—Lys—Ser—Lys—Ala—Val—Glu—Gln—Ile—Lys—Asn—Ala—Phe—Asn—Lys—Leu—Gln—Glu—Lys—Gly—Ile—Tyr—Lys—Ala—Met—Ser—Glu—Phe—Asp—Ile—Phe—Ile—Asn—Tyr—Ile—Glu—Ala—Tyr—Met—Thr—Ile—Lys—Ala—Arg. |

8. The composition of claim 6, in an implantable drug delivery system.

9. The composition of claim 6, in a unit dosage injectable form.

10. The composition of claim 9, wherein said unit dosage is at least 1 μg/kg.

11. The composition of claim 6, wherein said carrier is selected from the group consisting of:

a) saline;

b) Ringer's solution;

c) dextrose solution; and d) Hank's solution.

12. The composition of claim 6, which includes a preservative.

13. The composition of claim 6, in a form suitable for parenteral administration.

14. A purified BCRF1 protein.

15. The protein of claim 14 which is capable of inhibiting the synthesis of interferon-γ(IFN-γ).

16. The recombinant protein of claim 14 expressed in a host selected from the group consisting of:

a) a bacterial host;

b) a yeast host;

c) an insect host; or d) a mammalian host.

17. The protein of claim 14, made in *E. coli*.

18. The protein of claim 17, wherein said protein is found in an inclusion body.

19. The protein of claim 14, made in a primate cell.

20. A protein capable of inhibiting the synthesis of interferon-γ selected from the group of mature proteins of an open reading frame defined by the amino acid sequence:

| |
|---|
| Met—Glu—Arg—Arg—Leu—Val—Val—Thr—Leu—Gln—Cys—Leu—Val—Leu—Leu—Tyr—Leu—Ala—Pro—Glu—Cys—Gly—Gly—Thr—Asp—Gln—Cys—Asp—Asn—Phe—Pro—Gln—Met—Leu—Arg—Asp—Leu—Arg—Asp—Ala—Phe—Ser—Ara—Val—Lys—Thr—Phe—Phe—Gln—Thr—Lys—Asp—Glu—Val—Asp—Asn—Leu—Leu—Leu—Lys—Glu—Ser—Leu—Leu—Glu—Asp—Phe—Lys—Gly—Tyr—Leu—Gly—Cys—Gln—Ala—Leu—Ser—Glu—Met—Ile—Gln—Phe—Tyr—Leu—Glu—Glu—Val—Met—Pro—Gln—Ala—Glu—Asn—Gln—Asp—Pro—Glu—Ala—Lys—Asp—His—Val—Asn—Ser—Leu—Gly—Glu—Asn—Leu—Lys—Thr—Leu—Arg—Leu—Arg—Leu—Arg—Arg—Cys—His—Arg—Phe—Leu—Pro—Cys—Glu—Asn—Lys—Ser—Lys—Ala—Val—Glu—Gln—Ile—Lys—Asn—Ala—Phe—Asn—Lys—Leu—Gln—Glu—Lys—Gly—Ile—Tyr—Lys—Ala—Met—Ser—Glu—Phe—Asp—Ile—Phe—Ile—Asn—Tyr—Ile—Glu—Ala—Tyr—Met—Thr—Ile—Lys—Ala—Arg. |

21. A BCRF1 protein defined by the amino acid sequence:

| |
|---|
| Thr—Asp—Gln—Cys—Asp—Asn—Phe—Pro—Gln—Met—Leu—Arg—Asp—Leu—Arg—Asp—Ala—Phe—Ser—Arg—Val—Lys—Thr—Phe—Phe—Gln—Thr—Lys—Asp—Glu—Val—Asp—Asn—Leu—Leu—Leu—Lys—Glu—Ser—Leu—Leu—Glu—Asp—Phe—Lys—Gly—Tyr—Leu—Gly—Cys—Gln—Ala—Leu—Ser—Glu—Met—Ile—Gln—Phe—Tyr—Leu—Glu—Glu—Val—Met—Pro—Gln—Ala—Glu—Asn—Gln—Asp—Pro—Glu—Ala—Lys—Asp—His—Val—Asn—Ser—Leu—Gly—Glu—Asn—Leu—Lys—Thr—Leu—Arg—Leu—Arg—Leu—Arg—Arg—Cys—His—Arg—Phe—Leu—Pro—Cys—Glu—Asn—Lys—Ser—Lys—Ala—Val—Glu—Gln—Ile—Lys—Asn—Ala—Phe—Asn—Lys—Leu—Gln—Glu—Lys—Gly—Ile—Tyr—Lys—Ala—Met—Ser—Glu—Phe—Asp—Ile—Phe—Ile—Asn—Tyr—Ile—Glu—Ala—Tyr—Met—Thr—Ile—Lys—Ala—Arg. |

* * * * *